United States Patent [19]

Truffer

[11] Patent Number: 5,316,020
[45] Date of Patent: May 31, 1994

[54] SNORING PREVENTION DEVICE

[76] Inventor: Ernest Truffer, Notre Dame des Marais 1, CH-3960 Sierre, Switzerland

[21] Appl. No.: 852,226

[22] PCT Filed: Sep. 30, 1991

[86] PCT No.: PCT/CH91/00204
§ 371 Date: May 28, 1992
§ 102(e) Date: May 28, 1992

[87] PCT Pub. No.: WO92/05752
PCT Pub. Date: Apr. 16, 1992

[30] Foreign Application Priority Data

Oct. 3, 1990 [CH] Switzerland ............ 3175/90

[51] Int. Cl.⁵ ............ A61F 5/56; A61C 5/14
[52] U.S. Cl. ............ 128/848; 128/861
[58] Field of Search ............ 128/848, 859–861, 128/62 A; 2/2

[56] References Cited

U.S. PATENT DOCUMENTS

| | | | |
|---|---|---|---|
| 1,674,336 | 6/1928 | King | 128/848 |
| 2,705,006 | 3/1955 | Cettel | 128/848 |
| 4,669,459 | 6/1987 | Spiewak | 128/848 |
| 4,715,368 | 12/1987 | George | 128/848 |
| 4,862,903 | 9/1989 | Campbell | 128/861 |
| 4,901,737 | 2/1990 | Toone | 128/848 |
| 5,003,994 | 4/1991 | Cook | 128/859 |
| 5,092,346 | 3/1992 | Hays | 128/848 |
| 5,117,816 | 6/1992 | Shapiro | 128/848 |

*Primary Examiner*—Michael A. Brown
*Attorney, Agent, or Firm*—Woodard, Emhardt, Naughton, Moriarty & McNett

[57] ABSTRACT

A device for preventing snoring stops pharyngeal snoring by making the jaw (7) and consequently the base of the tongue (4) project forwards thereby creating an adequate opening of the pharyngeal canal (5). The device also prevents velar snoring by holding the mouth closed by means of hooks (11) positioned both towards the upper dental arch and towards the lower dental arch.

1 Claim, 3 Drawing Sheets

SNORING PREVENTION DEVICE

The present invention relates to a snoring prevention device.

Two types of snoring are distinguished, depending on the localization of their origin. The first type of snoring, velar snoring, is produced by the vibration of all the structures of the soft palate, i.e. the velum, the anterior and posterior arches of the tonsils and the uvula. Velar snoring results from a vibration of the soft palate created by the inspiratory flow of air both nasal and oral, which makes the soft palate wave like a flag. The sound intensity of these vibrations is accentuated by the opening of the buccal cavity which acts as a sound box.

The second type, i.e: pharyngeal snoring, is a sort of rale, of rattle, and even horn whistling. It is caused by the partial obstruction of the oropharyngeal isthmus by the base of the tongue with, now and again, its total occlusion by this tongue base becoming jammed against the posterior wall of the pharynx, according to the laws of fluid dynamics, thus causing cessation of breathing (apnoea), which constitutes the sleep apnoea syndrome (SAS). Here obstructive sleep apnoea is involved, as opposed to central sleep apnoea, which has a cerebral origin.

It should be stated that the two types of snoring described above may easily be combined in the same individual.

Snoring, which is always a nuisance for any person nearby, is not inoffensive for the snorer himself, primarily in the case of pharyngeal snoring accompanied by obstructive apnoea.

For some years there have been surgical techniques for correcting this snoring. However, the maxillary surgery which pharyngeal snoring requires is major surgery, with the operation lasting several hours and the uvulo-palatopharyngoplasty (UPPP) correcting velar snoring is not without drawbacks. This explains the popularity of prostheses and other preventative devices.

The device proposed in U.S. Pat. No. 4,669,459 very particularly relates to velar snoring and makes use of a lozenge which is meant to rest on the soft palate so as to prevent it from starting to vibrate. The device is fixed by means of dental hooks. In principle it has no effect on pharyngeal snoring.

Some devices tackle pharyngeal snoring and, starting from the same fact that this type of snoring is associated with a retrognathia of the lower jaw, they tend to cause an advancement of the lower jaw so as to separate the base of the tongue from the posterior pharyngeal wall and thus extend the laryngeal isthmus. These devices have shapes which resemble gum shields, such as used by sportsmen, boxers in particular. Within this family of devices it may be noted that the majority of them offers a sort of respiratory duct, a little like the mouthpiece of a snorkel. Such devices are described in the following patents: U.S. Pat. No. 3,434,470; U.S Pat. No. 1,674,336; GB 1 569 129; DE PS 23 20 501 or also EP 0 312 368.

Other devices, on the other hand, concentrate on pulling the base of the tongue forwards, not by acting on the lower jaw, but by acting directly on the tongue. Thus, in patent U.S. Pat No. 3,132,647, a sort of spoon rests directly on the tongue. Finally, in U.S. Pat. No. 4,304,227, the tongue is introduced into a housing and remains there confined and pulled forwards by suction, a little as children do when introducing their tongue into the neck of a bottle.

To sum up, the devices already known may only tackle one of the two types of snoring described above. Some of them do not appear to be particularly comfortable to wear. It is not necessary to dwell on the shortcomings of the known devices, as every one can very well imagine the sensation created by these devices when worn. Doubtless in some cases snoring is overcome by the lack of sleep.

It will also be noted that no known device is able to keep the snorer's mouth shut, even if in the last patent cited oral respiration is prevented or proclaimed as such.

The object of the present invention is to propose a device capable of eliminating both types of snoring, either separately, or simultaneously, with it being stated that this device assumes that nasal respiration is possible. In other terms, the device according to the invention can in no way cover the case in which the snorer has a blocked nose.

The definition of the anti-snoring device according to the invention is given in claim 1. Embodiments are defined in the claims subordinate to claim 1.

A device according to the invention is described below by way of example with reference to the drawings, in which.

Figure 1:
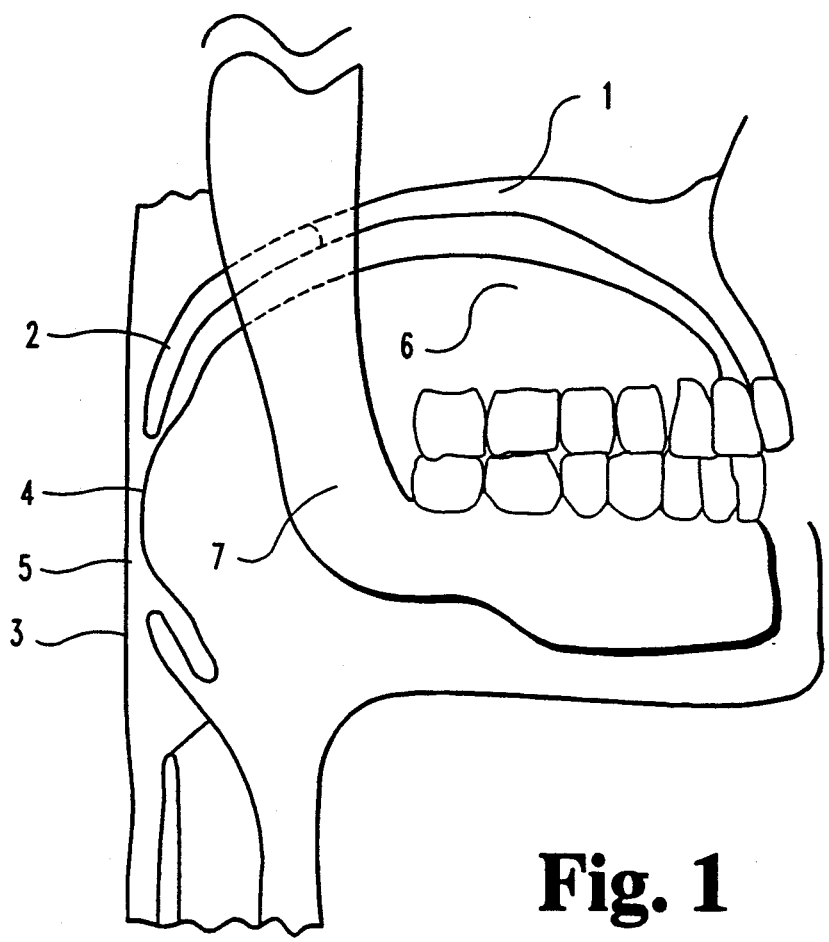
FIG. 1 shows a sagittal section of the buccopharyngeal region and is used as a basis to explain the two types of snoring.

By studying FIG. 1 the bony palate 1, extended by the soft palate and the uvula 3, will be distinguished. The pharyngeal wall 3 and the base of the tongue 4, which between them describe a space, the oropharyngeal isthmus 5, are also seen.

The configuration illustrated in FIG. 1, enables the two types of snoring to be described. Velar snoring is produced by the flow of two flows of inspirational air. The nasal flow circulates over the upper surface of the soft palate and of the uvula 2. The buccal flow circulates between the lower surface of the palate and the upper part 6 of the tongue. These two flows, which arrive from both sides of the uvula and of the soft palate 2, make them vibrate, which causes sound waves which create the snoring. The soundbox which is formed by the buccal cavity, amplifies these sound waves and makes them louder.

Pharyngeal snoring is caused by the narrowness of the oropharyngeal isthmus 5. In fact, the passage of the air in such a narrow duct causes a rale, or even a horn whistling. Finally the complete coming together of the base of the tongue and of the pharyngeal wall 3 causes obstructive apnoea.

Figure 2:
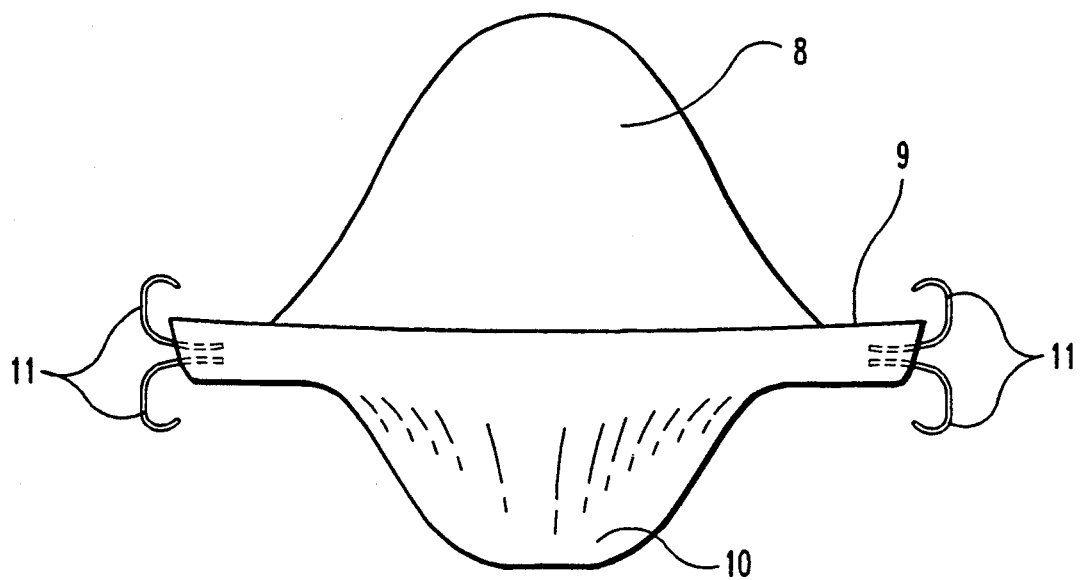
FIG. 2 shows a front view of the device according to the invention.
Figure 3:
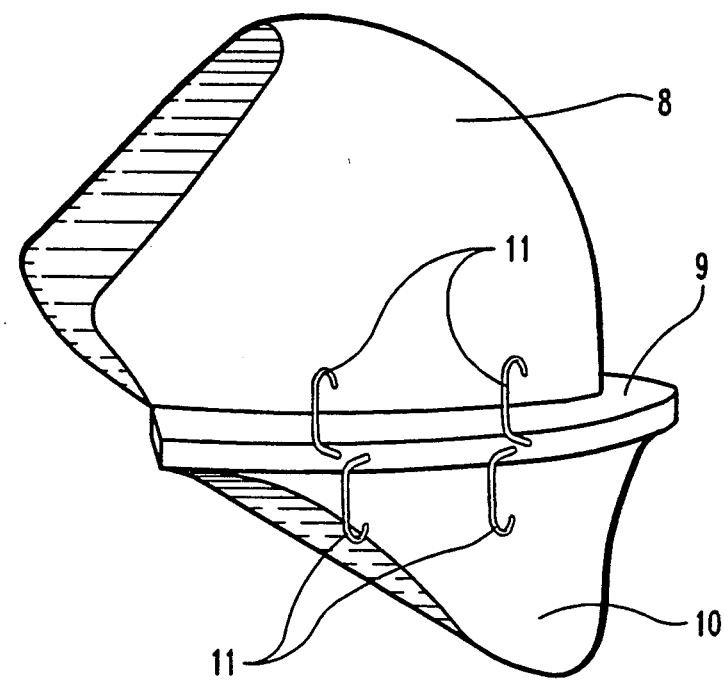
FIG. 3 shows a side view of the device according to the invention.
Figure 4:
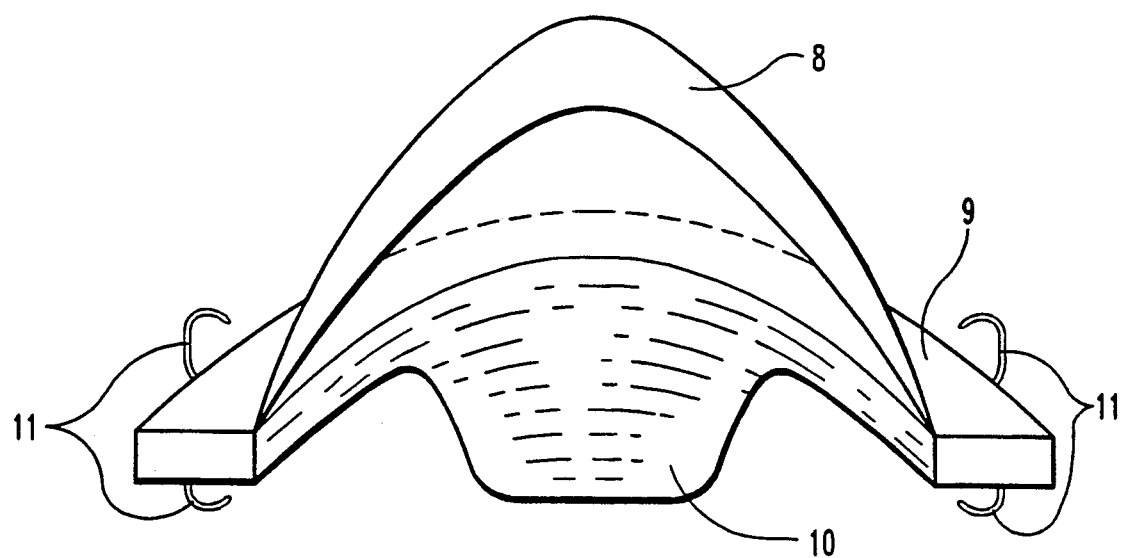
FIG. 4 shows the device according to the invention, seen from the rear.

Although the essential part of the device is in fact made from a single piece and from the same material, a hard plastic, it is advisable to distinguish three parts, each of which has its own function. With reference to FIGS. 2 to 4, firstly the upper part 8 of the device is distinguished.

This part is meant to rest on the bony palate and to ensure the positioning of the device in the mouth. For this purpose it is constructed from an impression of the palate and made from hard plastic. Thus the upper part 8 of the device perfectly fits the palate.

The second part is the median support part of the device. As has been mentioned, this median part 9 is integral with the two other parts. It is shaped as a lateral protruding edge on which the upper and lower dental arches come to be positioned. Hence the necessity of the making a prior impression of the two dental arches so as to model the median support part 9 depending firstly on the inherent characteristics of the person who will wear the device and secondly on the degree of projection wanted for the lower jaw, which, once determined, will also by definition apply for the third part of the device. At this stage in the description it should be stressed that, contrary to most of the known devices, the device according to the invention does not propose to house dental arches in U-shaped channels or grooves. Therefore in the device according to the invention there is no component which is inserted between the teeth and the lips.

A third part or antero-inferior part 10 keeps the lower jaw forward by being placed behind the anterior teeth of the lower jaw. It can be seen better on FIG. 4. It is important to note that the force necessary to project the lower jaw forward is not transmitted thereto by just the anterior teeth of the lower dental arch. In fact, all the teeth share in the effort and this is one of the original features of the device. In fact, if the dental arches are kept in close contact with their respective impressions, each tooth offers resistance to sliding and to the return to the natural configuration as illustrated by FIG. 1. Of course, by simply pressing the jaws against one another, the wearer may achieve this effect. But he certainly will not do this once he is asleep. The device according to the invention as it happens allows this effect to be continuously produced by itself ensuring that the mouth is kept in the closed position. The advantage of this situation is, as stated above, that oral respiration is in fact suppressed. The use of dental hooks 11 allows to keep the mouth in the closed position. The number, the shape and the arrangement of the hooks depend on the condition of the mouth of the wearer of the device. As regards the design of the hooks, in all their details, the usual technique of dental technicians will be relied on. It should be stressed that the use of hooks has been proposed in one of the patents forming the prior art, but it will be noted that their function is by no means to produce the closing of the mouth; moreover they are only applied to the upper jaw, which clearly prevents the effect sought in the present invention. It will also be noted that the use of U-shaped grooves, which have already been mentioned, excludes de facto the use of hooks.

FIG. 3 enables one to become more aware of the shapes and volumes of the various parts of the device and enables one to understand that the force of contraction exerted by the lower jaw is not just expressed in a forwards-backwards direction but is partially transformed into a vertical component which rests on the hard palate by means of the upper part 8.

FIG. 4 shows the device seen from the rear and enables one to note that the tongue is free in the mouth and has at its disposal a space which is roughly equal to its natural space.

Figure 5:
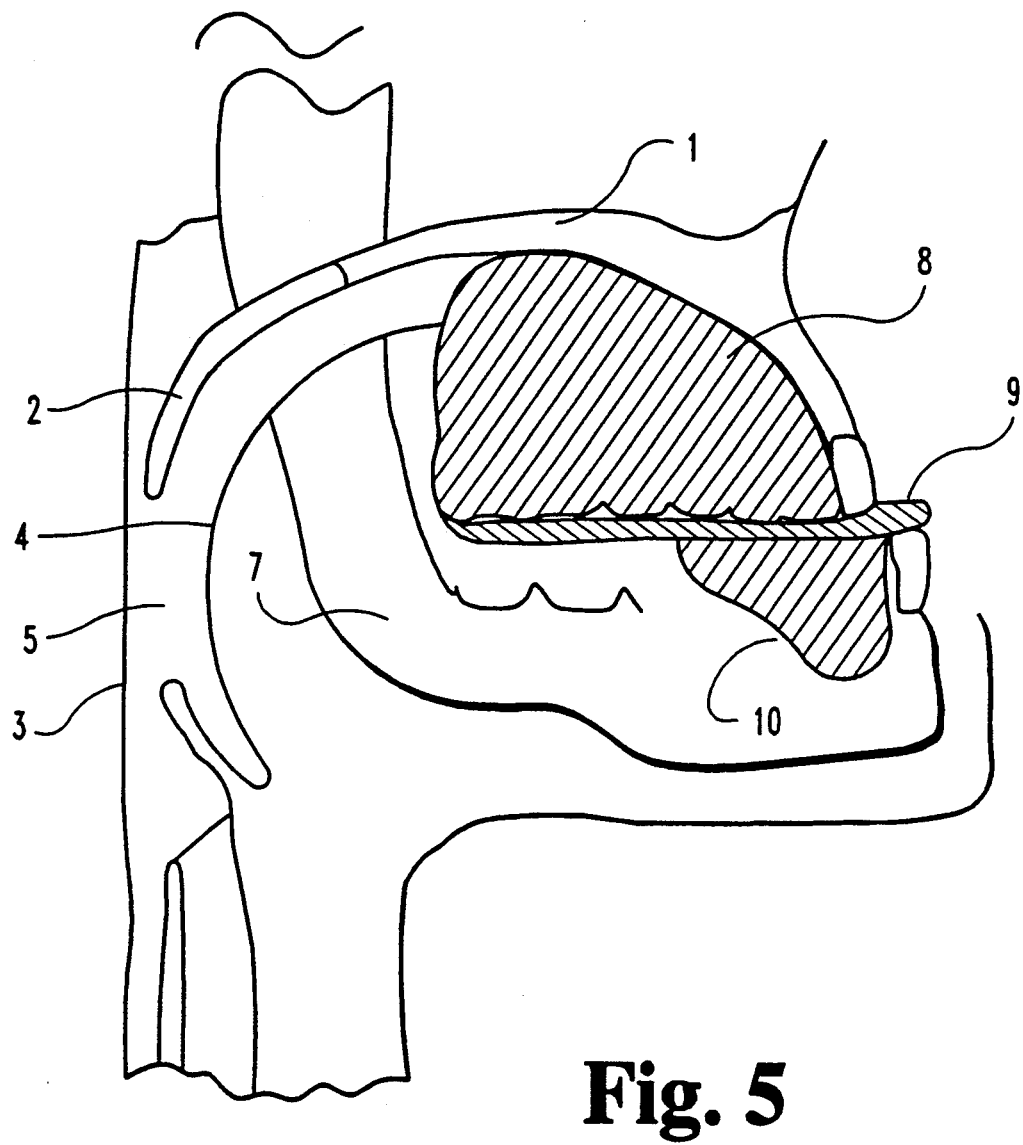
FIG. 5 shows a section similar to that in FIG. 1, but in the configuration which the device achieves once it is in position.

FIG. 5 enables the modifications produced by wearing the device according to the invention to be seen. It will firstly be noted that the lower jaw 7 is subject to subluxation and pushed forwards. As a result the base of the tongue 4 is also pushed forwards and is thus at a distance from the pharyngeal wall 3, thus producing a widening of the oropharyngeal isthmus 5, which is proportional to this projection. It will be noted that the uvula 2 is also better cleared.

Pharyngeal snoring is thus eliminated, as the oropharyngeal isthmus again has adequate dimensions to suppress the rattle and the risk of apnoea.

Velar snoring is also eliminated as, because the mouth is kept closed by the application of the upper and lower teeth on the median part, which are locked into this position by the hooks, there is no longer any oral inspiratory flow and thus no vibration of the soft palate either. The fact that the mouth is closed and kept closed has the second consequence that it can no longer act as a sound box. Finally, if there were any residual vibrations, their resonance would be stifled by buccal occlusion.

The device according to the invention of course assumes that three conditions are met: i.e. the possibility of breathing through one's nose, the existence of an adequate number of teeth for fixing the device into position and finally an adequate laxity of the articulation of the jaw. This laxity is determined by the capacity and the extent of movement, in the antero-posterior direction, of the lower jaw.

Given the specific character of the maxillo-dental morphology of each individual, it is not possible to obtain a standard device. The construction of the device requires dental impressions to be taken and, consequently, collaboration with the doctor-dentist, who will proceed as for a dental prosthesis. Once the device has been made according to instructions and using the prosthetic dental technique, the patient will be able to place it in his mouth and remove it as with any detachable dental prosthesis.

The tests carried out show that the device, after the initial period of adaptation, is generally tolerated well and is only slightly annoying, but this can be easily overcome. Case histories, over a period of up to five years in some patients, have not shown any deterioration in the tooth enamel nor trouble with the bite, nor with the implantation of teeth nor with the temporomaxillary articulation.

The necessary conditions of use being taken into account, the advantages of the device according to the invention are essentially that it totally suppresses the two types of snoring, and does this simultaneously, if necessary. On the other hand, the device is designed so as to have the most discrete presence possible in the mouth thanks to the fact that the necessary space between the dental arches is reduced to the strict minimum which represents the median part. This characteristic primarily results from the fact that dental arches are not housed in U-shaped grooves and secondly from the fact that it does not have any respiratory canal. The realization of the device certainly requires the services of specialists in dentistry, which has a bearing on its price. However the device makes use of well-known and reliable dental techniques which guarantee a result which is perfectly adapted to the person concerned and is no more annoying than any other dental prosthesis. Finally, the device enables the grinding of teeth to be suppressed.

I claim:
1. A snoring prevention device, comprising:
a one piece mouthpiece without an air aperture, having an upper element configured to rest on the wearer's bony palate, a median element having a lateral protruding edge to receive upper and lower negative impressions of the wearer's upper and lower teeth, and a lower element configured and disposed to force the wearer's lower jaw into a position forward of the wearer's upper jaw; and
retention means for attaching the device within the wearer's mouth and for keeping the wearer's mouth closed when the device is in place, whereby the device prevents any mouth breathing by the wearer when the device is in place.

* * * * *